(12) United States Patent
Walsh et al.

(10) Patent No.: US 9,664,598 B2
(45) Date of Patent: May 30, 2017

(54) MICROFLUIDIC CONTAMINANT TRAP FOR TRAPPING CONTAMINANTS IN GAS CHROMATOGRAPHY

(71) Applicant: AGILENT TECHNOLOGIES, INC., Loveland, CO (US)

(72) Inventors: George P. Walsh, Wilmington, DE (US); Rebecca A. Veeneman, Newark, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 606 days.

(21) Appl. No.: 14/057,022

(22) Filed: Oct. 18, 2013

(65) Prior Publication Data

US 2015/0107332 A1    Apr. 23, 2015

(51) Int. Cl.
| | |
|---|---|
| *G01N 30/14* | (2006.01) |
| *G01N 30/02* | (2006.01) |
| *G01N 30/60* | (2006.01) |
| *G01N 1/22* | (2006.01) |

(52) U.S. Cl.
CPC .............. *G01N 1/22* (2013.01); *G01N 30/02* (2013.01); *G01N 30/14* (2013.01); *G01N 2030/025* (2013.01)

(58) Field of Classification Search
CPC ............... G01N 30/6095; G01N 1/22; G01N 2030/025; G01N 30/02; G01N 2030/143; G01N 30/14
See application file for complete search history.

(56) References Cited

U.S. PATENT DOCUMENTS

| | | | |
|---|---|---|---|
| 3,581,573 A | 6/1971 | Purcell et al. | |
| 4,242,227 A * | 12/1980 | Nestrick | C08G 83/001 |
| | | | 210/198.2 |
| 4,376,641 A | 3/1983 | Nestrick et al. | |
| 4,532,150 A | 7/1985 | Endo et al. | |
| 4,985,625 A | 1/1991 | Hurst | |
| 5,006,315 A | 4/1991 | Maroulis et al. | |

(Continued)

FOREIGN PATENT DOCUMENTS

| | | | |
|---|---|---|---|
| CN | WO 0011463 A1 * | 3/2000 | ............. G01N 30/56 |
| JP | H1151920 | 2/1999 | |

(Continued)

OTHER PUBLICATIONS

"IC Trap Columns" Dionex Corporation. 2011. Accessed online at <https://web.archive.org/web/20110716053538/http://www.dionex.com/en-us/products/columns/ic-rfic/trap/lp-73277.html>.*

(Continued)

*Primary Examiner* — Lisa Caputo
*Assistant Examiner* — Punam Roy

(57) ABSTRACT

Microfluidic contaminant traps of certain representative embodiments illustratively comprise: an inlet configured to connect directly or indirectly to a sample inlet of a gas chromatography (GC) system; an outlet configured to connect directly to an inlet of a GC column or indirectly to the GC column via another fluidic component; an interlayer comprising a channel; an upper layer disposed over and bonded to the interlayer; and a coating disposed over the channel. The coating reduces interactions of analytes from a sample provided at the inlet of the microfluidic contaminant trap with the microfluidic contaminant trap.

20 Claims, 9 Drawing Sheets

(56) References Cited

U.S. PATENT DOCUMENTS

| | | | |
|---|---|---|---|
| 5,123,276 A * | 6/1992 | Hartman | G01N 1/405 73/23.41 |
| 5,261,937 A * | 11/1993 | Jiang | B01D 46/00 73/23.41 |
| 5,338,448 A | 8/1994 | Gjerde | |
| 5,447,556 A * | 9/1995 | Pleil | G01N 30/12 95/87 |
| 5,547,497 A | 8/1996 | Klemp et al. | |
| 5,567,868 A | 10/1996 | Craig et al. | |
| 5,686,656 A * | 11/1997 | Amirav | G01N 30/12 73/23.41 |
| 5,686,657 A | 11/1997 | Craig et al. | |
| 5,720,798 A | 2/1998 | Nickerson et al. | |
| 5,792,943 A | 8/1998 | Craig | |
| 5,888,390 A | 3/1999 | Craig | |
| 5,988,703 A | 11/1999 | Craig | |
| 5,997,708 A | 12/1999 | Craig | |
| 6,089,617 A | 7/2000 | Craig et al. | |
| 6,386,014 B1 * | 5/2002 | Butch | G01N 30/6095 73/23.22 |
| 6,444,326 B1 | 9/2002 | Smith | |
| 6,457,236 B1 | 10/2002 | White et al. | |
| 6,612,153 B2 | 9/2003 | White et al. | |
| 6,679,989 B2 | 1/2004 | Willis et al. | |
| 6,709,027 B2 | 3/2004 | Rittenhouse | |
| 6,749,749 B2 | 6/2004 | Xie et al. | |
| 6,783,871 B2 | 8/2004 | Sheng | |
| 6,966,212 B2 | 11/2005 | Klee et al. | |
| 7,074,327 B2 * | 7/2006 | O'Connor | B01L 3/5025 210/143 |
| 7,128,876 B2 | 10/2006 | Yin et al. | |
| 7,287,441 B2 | 10/2007 | Klee et al. | |
| 7,316,730 B2 | 1/2008 | Rightnour et al. | |
| 7,384,457 B2 | 6/2008 | Emmons et al. | |
| 7,430,893 B2 | 10/2008 | Grayfer et al. | |
| 7,451,634 B2 * | 11/2008 | Gamache | G01N 30/14 73/23.35 |
| 7,600,439 B1 | 10/2009 | Patterson et al. | |
| 7,608,818 B2 * | 10/2009 | Miller | G01N 27/624 250/281 |
| 7,811,452 B2 | 10/2010 | Yin et al. | |
| 8,123,841 B2 | 2/2012 | Masel et al. | |
| 8,132,443 B2 * | 3/2012 | McGill | B01J 20/205 73/23.39 |
| 8,152,908 B2 * | 4/2012 | Masel | G01N 30/6095 210/198.2 |
| 8,414,832 B1 | 4/2013 | Roques et al. | |
| 8,815,177 B2 * | 8/2014 | Perroud | B01F 3/0807 422/503 |
| 8,931,356 B2 | 1/2015 | Michienzi et al. | |
| 2002/0024662 A1 * | 2/2002 | Ueno | G01N 21/0332 356/246 |
| 2004/0238052 A1 * | 12/2004 | Karp | B01F 5/0471 137/822 |
| 2005/0042139 A1 * | 2/2005 | Bonne | G01N 1/24 422/68.1 |
| 2005/0252275 A1 * | 11/2005 | Kita | G01N 33/0031 73/23.34 |
| 2006/0038402 A1 | 2/2006 | Norman et al. | |
| 2006/0144237 A1 * | 7/2006 | Liang | G01N 30/6095 96/101 |
| 2007/0000828 A1 | 1/2007 | Norman et al. | |
| 2007/0029477 A1 * | 2/2007 | Miller | G01N 27/624 250/290 |
| 2007/0029791 A1 | 2/2007 | Haertl | |
| 2007/0256474 A1 * | 11/2007 | Paakkanen | B01D 53/02 73/23.37 |
| 2008/0121016 A1 * | 5/2008 | Shah | G01N 30/88 73/23.42 |
| 2008/0185057 A1 * | 8/2008 | Prakash | F16K 99/0001 137/594 |
| 2009/0001008 A1 | 1/2009 | Deorkar et al. | |
| 2009/0065415 A1 | 3/2009 | Vetter et al. | |
| 2009/0189064 A1 * | 7/2009 | Miller | G01N 27/624 250/282 |
| 2009/0211452 A1 * | 8/2009 | Masel | G01N 30/6095 96/101 |
| 2009/0321356 A1 * | 12/2009 | Gerhardt | G01N 30/6095 210/656 |
| 2010/0186524 A1 * | 7/2010 | Ariessohn | G01N 1/2202 73/863.22 |
| 2010/0262034 A1 * | 10/2010 | Kawata | A61B 5/097 600/532 |
| 2010/0282077 A1 * | 11/2010 | Jones | G01N 30/12 95/25 |
| 2011/0023581 A1 | 2/2011 | Chou et al. | |
| 2011/0143952 A1 * | 6/2011 | Lewis | G01N 30/463 506/8 |
| 2012/0118049 A1 * | 5/2012 | Tipler | G01N 30/72 73/61.56 |
| 2013/0125564 A1 | 5/2013 | Booth | |
| 2013/0126021 A1 * | 5/2013 | Hobbs | G01N 30/6039 137/557 |
| 2013/0276512 A1 * | 10/2013 | Bae | G01N 30/02 73/23.35 |
| 2014/0150660 A1 * | 6/2014 | Klee | G01N 30/60 96/106 |
| 2014/0170641 A1 * | 6/2014 | Macemon | G01N 1/00 435/5 |
| 2015/0078962 A1 * | 3/2015 | Fogwill | G01N 30/68 422/54 |
| 2015/0101393 A1 * | 4/2015 | Fogwill | G01F 1/76 73/23.31 |
| 2015/0122365 A1 * | 5/2015 | Carr | C23C 16/045 138/145 |
| 2015/0212053 A1 * | 7/2015 | Wang | G01N 30/30 73/23.4 |
| 2015/0338382 A1 * | 11/2015 | Guan | G01N 30/28 73/23.42 |
| 2016/0018366 A1 * | 1/2016 | Fogwill | G01N 30/32 73/863.11 |
| 2016/0018367 A1 * | 1/2016 | Fogwill | G01N 30/32 210/177 |

FOREIGN PATENT DOCUMENTS

| | | | | |
|---|---|---|---|---|
| WO | WO 2004029079 A1 * | 4/2004 | | C07K 1/22 |
| WO | WO2004051258 | 6/2004 | | |

OTHER PUBLICATIONS

Sandra, Patrick, et al. "Development of a Miniature Gas Chromatograph (mu CAD) with Sample Enrichment, Programmed Temperature GC and Plasma Emission Detection (PED)." LC GC Europe 22.3 (2009): 112. Accessed online at <http://www.chromatographyonline.com/print/226559?page=full> on Jan. 26, 2017.*

Search Report mailed Mar. 18, 2015 in UK Application No. GB1417845.3.

Agilent Technologies, Agilent 7890A, "Gas Chromatograph: Maintaining Your GC.", 5th edition, published May 2011.

Co-pending U.S. Appl. No. 13/660,273, filed Oct. 5, 2012.

Co-pending U.S. Appl. No. 13/718,061, filed Dec. 18, 2012.

"Deactivated Fused Silica Tubing", Restek Corporation catalog.

Scientific Instrument Services, Inc. (SIS), SIS GC Cryo-Traps, website product page viewed on Nov. 11, 2016.

PerkinElmer, TurboMatrix Headspace and Headspace Trap Samplers for GC brochure, May 2, 2015.

Shimadzu, Headspace Samplers HS-20 Series website product page, viewed on Nov. 11, 2016.

Tekmar Lumin PurgeTrap Brochure, Apr. 2016.

Restek, Glass Indicating Oxygen Trap literature, May 18, 2016.

Alelyunas, et al., Exploring Extra Sensitivity Using ionKey/MS with the Xevo G2-XS Q-Tof HRMS for Small Molecule Pharmaceutical Analysis in Human Plasma, Apr. 2015.

Optimize Technologies, Application Note #101, trapping: a general guide, Jan. 31, 2012.

(56) References Cited

OTHER PUBLICATIONS

Agilent Technologies, Agilent 1260 Infinity HPLC-Chip/MS System brochure, Sep. 1, 2010.
Jay S. Johnson, Considerations in Developing a Protoype Microfluidic Trapping Column to Improve Mass and Volume Capacity in an Integrated LC/MS System (poster), Waters Corporation 2012.

* cited by examiner

MICROFLUIDIC CONTAMINANT TRAP FOR TRAPPING CONTAMINANTS IN GAS CHROMATOGRAPHY

BACKGROUND

Gas chromatography (GC) is used to analyze and detect the presence of many different substances in a gaseous or vaporized sample. The function of a gas chromatograph is to separate the components of a chemical sample and detect the presence and frequently the quantity of those components. The separation is frequently accomplished using a capillary column. This column is essentially a piece of fused silica tubing with a coating on the inside that interacts with the sample to separate the components. The dimensions of this column vary, but typical inside diameters range from 100 microns to 530 microns. Typical lengths range from 5 meters to 60 meters.

If the user is analyzing a sample that contains relatively non-volatile components, those components will deposit on the inner walls of the column, contaminating the column and possibly degrading its performance. If enough degradation occurs after repeated analyses, the user will have to take action to mitigate if not eliminate the impact of contaminants in the column.

Known methods to address the ill-effects of contaminants in the GC system include repeatedly trimming the contaminated part of the column and/or replacing the column. Alternatively, a sacrificial section of a column can be used. Such a sacrificial column, which is typically referred to as either a "retention gap", "pre-column," or a "guard column," can be either user created (e.g., using cut pieces of deactivated fused silica capillary along with column connections), or purchased as a complete product. Still alternatively, the column may be backflushed to remove sample components that are not of analytical interest and that are slow moving in the column at the analysis temperature.

Many of the above-noted solutions require the user to handle a fused silica capillary to trap the contaminants. The capillary must be carefully installed into the inlet for the GC system to work properly. Steps of a proper installation include trimming the capillary to the required length while creating a clean, square end on it; avoiding or eliminating contamination of the inside or outside of the capillary; positioning the capillary at the correct depth into the inlet; creating a leak tight seal to the capillary; and creating a leak tight seal to the inlet. As can be appreciated, the complexity of installing the capillary after, for example, trimming the column, and the ultimate quality of the connection of the capillary to the inlet can be less than desirable or acceptable.

What is needed, therefore, is an apparatus that overcomes at least the shortcomings of known structures described above.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

Figure 1:
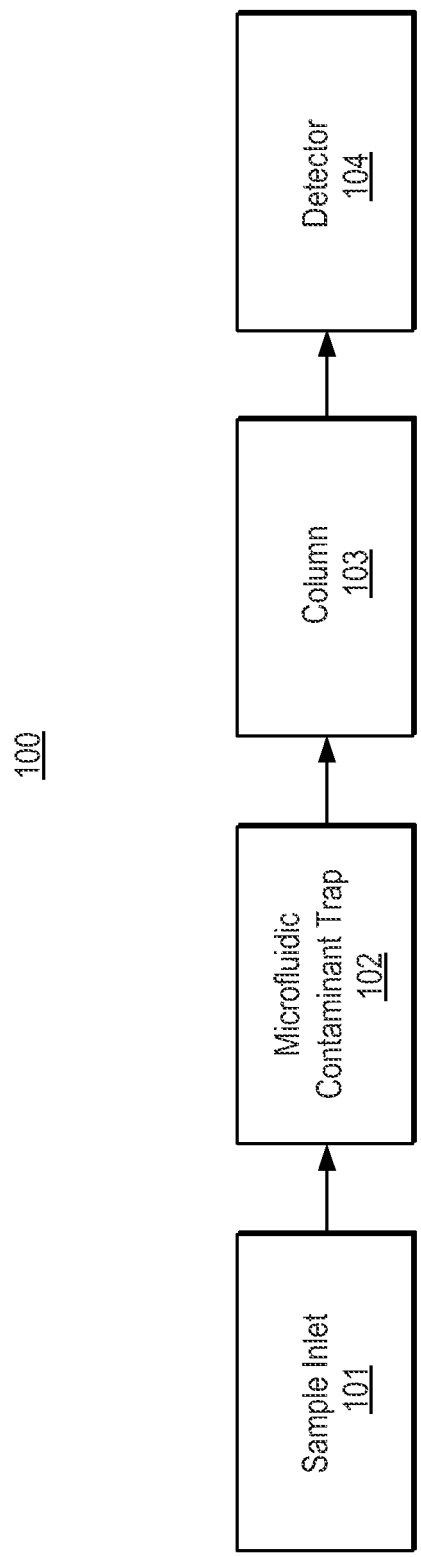
FIG. 1 is a simplified block diagram of a GC system in accordance with a representative embodiment.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms 'a', 'an' and 'the' include both singular and plural referents, unless the context clearly dictates otherwise. Thus, for example, 'a device' includes one device and plural devices.

As used in the specification and appended claims, and in addition to their ordinary meanings, the terms 'substantial' or 'substantially' mean to with acceptable limits or degree. For example, 'substantially cancelled' means that one skilled in the art would consider the cancellation to be acceptable.

As used in the specification and the appended claims and in addition to its ordinary meaning, the term 'approximately' means to within an acceptable limit or amount to one having ordinary skill in the art. For example, 'approximately the same' means that one of ordinary skill in the art would consider the items being compared to be the same.

DETAILED DESCRIPTION

In the following detailed description, for purposes of explanation and not limitation, representative embodiments disclosing specific details are set forth in order to provide a thorough understanding of the present teachings. Descriptions of known systems, devices, materials, methods of operation and methods of manufacture may be omitted so as to avoid obscuring the description of the example embodiments. Nonetheless, systems, devices, materials, and methods that are within the purview of one of ordinary skill in the art may be used in accordance with the representative embodiments.

Generally, it is understood that the drawings and the various elements depicted therein are not drawn to scale. Further, relative terms, such as "above," "below," "top," "bottom," "upper," "lower," "left," "right," "vertical" and "horizontal," are used to describe the various elements' relationships to one another, as illustrated in the accompanying drawings. It is understood that these relative terms are intended to encompass different orientations of the microfluidic contaminant traps and/or elements in addition to the orientation depicted in the drawings. For example, if the microfluidic contaminant trap were inverted with respect to the view in the drawings, an element described as "above" another element, for example, would now be "below" that element. Likewise, if the device were rotated 90 degrees with respect to the view in the drawings, an element described as "vertical," for example, would now be "horizontal."

Representative embodiments are directed to a microfluidic contaminant trap. Microfluidic contaminant traps of certain representative embodiments illustratively comprise: an inlet configured to connect directly or indirectly to a sample inlet of a gas chromatography (GC) system; an outlet configured to connect directly to an inlet of a GC column or indirectly to the GC column via another fluidic component; an interlayer comprising a channel; an upper layer disposed over and bonded to the interlayer; and a coating disposed over the channel. The coating reduces interactions of analytes from a sample provided at the inlet of the microfluidic contaminant trap with the microfluidic contaminant trap.

In another representative embodiment, a microfluidic contaminant trap comprises: an inlet configured to connect directly or indirectly to a sample inlet of a gas chromatography (GC) system; an outlet configured to connect to an inlet of a GC column or indirectly to the GC column via another fluidic component; a first interlayer comprising a first channel; and a first coating disposed over the first channel. The first coating reduces interactions of analytes from a sample provided at the inlet of the microfluidic contaminant trap. The microfluidic contaminant trap also comprises a second interlayer comprising a second channel. The first channel is in fluid communication with the second channel. The microfluidic contaminant trap also comprises a second coating disposed over the second channel. The second coating reduces interactions of analytes from a sample provided at the inlet of the microfluidic contaminant trap with the microfluidic contaminant trap. The microfluidic contaminant trap also comprises an upper layer disposed over the first interlayer; a middle layer disposed between a lower surface of the first interlayer and above an upper surface of the second interlayer; and a lower layer disposed beneath the second interlayer. The upper layer and the middle layer are configured to seal the first channel and the middle layer and the lower layer are configured to seal the second channel.

As will be appreciated by one having ordinary skill in the art upon review of the present application, among other benefits compared to known GC systems that include, for example the need to trim and reinstall a column, or to replace a guard column or to install a new column, the microfluidic contaminant trap may be connected between a sample inlet and a column without the need to provide a trimmed, clean face of a proper length to the column. Furthermore, unlike known GC systems, which require connections to make two simultaneous connections (column to ferrule and ferrule to inlet), two independent connections are made using the microfluidic trap of the representative embodiments (inlet to trap and trap to GC system). In these representative embodiments, this seal is a face-to-face seal, which is less prone to over tightening than connections in other known GC systems. Furthermore, these embodiments have a smaller footprint than an equivalent piece of fused silica. For example, a 793 mm long section of 500 μm×500 μm channel in a microfluidic device can be placed in a 45 mm×20 mm×1 mm space. A 793 mm section of 530 μm fused silica capillary cannot be wrapped smaller than a 130 mm diameter without significant risk of the fused silica fracturing. Furthermore, the microfluidic contaminant trap of the present teachings is far easier to handle than the capillary column and without touching of sealing surfaces. As such, the microfluidic contaminant traps of the representative embodiments are less prone to GC system contamination by a user. Moreover, the planar geometry and connections of the microfluidic contaminant traps of the representative embodiments facilitate temperature control of the microfluidic trap independently of the sample inlet and column. This facilitation is due to two characteristics of a planar structure, a high ratio of surface area to volume as well as a minimized distance from the outer surface to the center of the structure. Finally, and as will become clearer as the description of the present teachings continues, the microfluidic contaminant traps of the representative embodiments are configured to be replaced when their effectiveness reaches an unacceptable limit. This replacement is facilitated by the comparatively easy and efficient face-seal connection of the microfluidic contaminant trap to the outlet of the sample inlet and to the inlet of the column. These and other benefits of the microfluidic contaminant traps of the present teachings are described more fully below in connection with representative embodiments.

FIG. 1 is a simplified block diagram of a GC system 100 in accordance with a representative embodiment. Many aspects of the GC system 100 are known to one of ordinary skill in the art. As such, details of certain known components of the GC system 100 are omitted. In certain instances representative examples of known components that may be implemented are noted, but are presented for illustration and are, in no way, intended to be limiting.

The GC system comprises a sample inlet 101, such as a split/splitless inlet. The sample inlet 101 is fluidly coupled to a microfluidic contaminant trap 102. The microfluidic contaminant trap 102 is fluidly coupled to a column 103, which may be one of a variety of columns useful in gas chromatography.

The column 103 separates the components of a chemical sample. The column 103 may be a capillary column comprising a piece of fused silica tubing (not shown) with a coating on the inner portions of the tubing that interacts with the sample from sample inlet 101 to separate the components of the chemical sample. The dimensions of this column 103 vary, but typical inside diameters range from 100 microns to 530 microns. Typical lengths range from 5 meters to 60 meters. As described in detail below in connection with representative embodiments, the contaminant trap 102 is a microfluidic contaminant trap configured to trap contaminants from the sample coming from the sample inlet 101 and to prevent the contaminants from reaching the column 103 by trapping them before they reach the exit of the trap.

The column 103 is connected to a detector 104, which detects the presence and frequently the quantity of the components separated by the column 103. Generally, the detector 104 is a known GC detector such as a flame ionization detector (FID), a mass spectrometer detector (MSD), a thermal conductivity detector (TCD), an electron capture detector (ECD), a nitrogen phosphorus detector (NPD), a sulfur chemiluminescence detector (SCD), a nitrogen chemiluminescence detector (NCD), a pulsed flame photometric detector (PFPD), or a helium ionization detector (HID). In accordance with a representative embodiment, the detector may be a flame photometric detector (FPD) such as described in commonly owned U.S. patent application Ser. No. 13/660,273, filed on Oct. 5, 2012 and entitled "Flame Photometric Detector;" and commonly owned U.S. patent application Ser. No. 13/718,061, filed on Dec. 18, 2012 and entitled "Chemiluminescent Detector having Coating to Reduce Excite Species Adsorption." The disclosures of commonly owned U.S. patent application Ser. No.

13/660,273 and commonly owned U.S. patent application Ser. No. 13/718,061 are specifically incorporated herein by reference. It is emphasized that the use of FPDs is merely illustrative, and many other detectors known to one of ordinary skill in the art are contemplated by the present teachings.

Figure 2A:
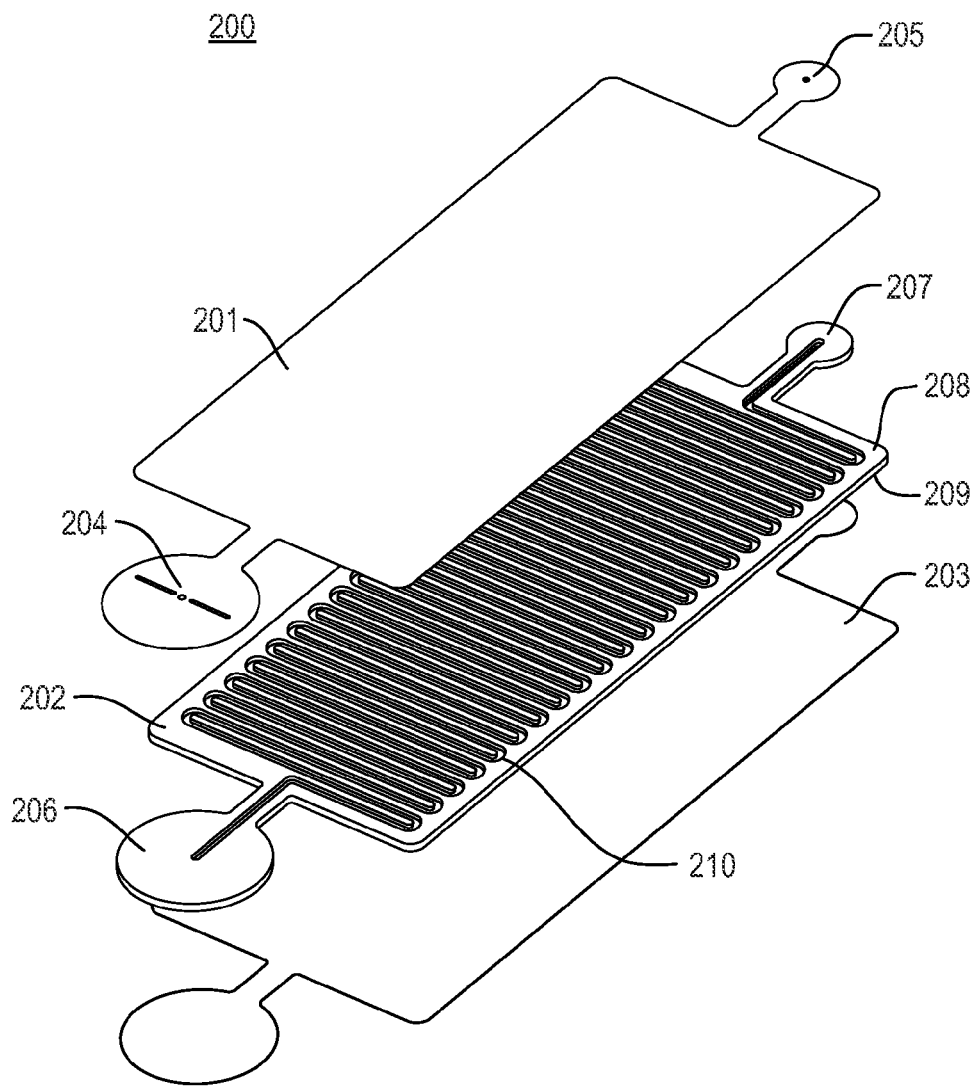
FIG. 2A is an exploded view of a microfluidic contaminant trap in accordance with a representative embodiment.

FIG. 2A is an exploded view of a microfluidic contaminant trap 200 in accordance with a representative embodiment. The microfluidic contaminant trap 200 comprises an upper layer 201, an interlayer 202 and a lower layer 203. The microfluidic contaminant trap 200 comprises an inlet 204 that is configured to be fluidly coupled either directly or indirectly to an outlet of a sample inlet (e.g., sample inlet 101). The microfluidic contaminant trap 200 also comprises an outlet 205 that is configured to be fluidly coupled either directly or indirectly to an inlet of a column of a GC system (e.g., column 103). In a representative embodiment, the sample inlet (e.g., sample inlet 101) is one of a split/splitless inlet (S/SL) or a multimode inlet (MMI) or other GC inlet type as known to one of ordinary skill in the art.

The inlet 204 is fluidly coupled to an interlayer inlet 206, and the outlet 205 is fluidly coupled to an interlayer outlet 207. The interlayer 202 comprises an interlayer upper surface 208 and an interlayer lower surface 209. A channel 210 is provided in the interlayer 202, and fluidly connects the interlayer inlet 206 to the interlayer outlet 207. As depicted in FIG. 2A, the channel 210 extends along a serpentine path between the interlayer inlet 206 and the interlayer outlet 207 to increase the distance through which the sample travels to maximize contaminant trapping. In accordance with a representative embodiment, a coating (not shown in FIG. 2A -See FIG. 4) is applied to all surfaces of the microfluidic contaminant trap 200 that come in contact with the sample. In a representative embodiment, the coating is a deactivation coating that is applied over the surfaces of the channel 210. Additionally, as applicable, the coating may be applied to all surfaces (e.g., the trapping features and exterior features (see representative embodiment of FIG. 4) of the microfluidic contaminant trap 200, to reduce the interaction of analytes of the sample with the surfaces with which the sample contacts. The deactivation coating comprises a selected chemical substance useful in reducing the interaction of the surface with analytes of interest within the sample. In a representative embodiment, the coating comprises a functionalized hydrogenated amorphous silicon surface, such as described, for example in U.S. Pat. No. 6,444,326, to Smith, The disclosure of U.S. Pat. No. 6,444,326 is specifically incorporated herein by reference. In a second representative embodiment, the coating comprises a silicon carbide surface, such as described, for example in U.S. Pat. No. 4,532,150, to Endo et al. The disclosure of U.S. Pat. No. 4,532,150 is specifically incorporated herein by reference. In a third representative embodiment, the coating comprises a siloxane surface, such as described, for example in U.S. Pat. No. 4,376,641, to Nestrick et al. The disclosure of U.S. Pat. No. 4,376,641 is specifically incorporated herein by reference. Illustratively, the deactivation coating may be a known silicon-based coating, a known siloxane, or other known polymeric, monomeric, or carbidecoatings. The coating is applied by known methods, and is applied after various components of the microfluidic contaminant trap are bonded to one another to ensure all surfaces that come into contact with the analytes of the sample are properly coated.

In certain representative embodiments, trapping features (not shown in FIG. 2A) are also provided in the channel to increase the surface area over which the sample flows, and thereby improve the degree of trapping of contaminants by the microfluidic contaminant trap 200. The trapping features serve to increase the surface area with which contaminants contact, beneficially spread the contaminants through the channel, and reduce interference between the contaminants and analytes of the sample. Fluid connections are made by forming conduits or through-holes between the inlet 204 and the interlayer inlet 206, and between the interlayer outlet 207 and the outlet 205, The fluid connections are made to provide a vertical connection (i.e., perpendicular to the planes of the upper layer 201, interlayer 202 and lower layer 203 depicted in FIG. 2A) from the inlet 204 to the interlayer inlet 206 and from the interlayer outlet 207 and the outlet 205. These channels can be formed using known methods based on the materials selected for the upper layer 201, interlayer 202 and lower layer 203. Moreover, these connections may be implemented as described in commonly owned U.S. Pat. Nos. 5,567,868, 5,720,798, 5,792,943, 5,997,708, 7,128,876 and 7,811,452, and as described in U.S. Pat. No. 8,123,841. The disclosures of these U.S. patents are specifically incorporated herein by reference. As alluded to above, one benefit of the microfluidic contaminant trap 200 of the representative embodiment is the ease and efficiency with which it is replaced when it becomes saturated by contaminants or otherwise reaches an unacceptable degree of efficiency. As such, in accordance with a representative embodiment, the microfluidic contaminant trap 200 may be a disposable element of GC system 100, and easily and efficiently replaced without compromising the integrity of the GC system as can occur using known traps and methods of use.

In a representative embodiment, the upper layer 201, the interlayer 202 and the lower layer 203 comprise stainless steel plates. The upper layer 201, interlayer 202 and lower layer 203 may be chemically etched to form the channel 210 and other microfluidic conduits and connections (e.g., interlayer inlet 206 and interlayer outlet 207) of the microfluidic contaminant trap 200. The upper layer 201, the interlayer 202 and the lower layer 203 are bonded together using known techniques of pressure and heat, for example, the method described in commonly-owned U.S. Pat. No. 6,783,871 to Sheng, the disclosure of which is specifically incorporated herein by reference.

In alternative embodiments at lower application temperatures, the upper layer 201, the interlayer 202 and the lower layer 203 comprise polyimide sheets that are laser ablated to form the channel 210 and other microfluidic conduits and connections. The upper layer 201, the interlayer 202 and the lower layer 203 may then be sealed by heat sealing.

In yet other alternative embodiments, the upper layer 201, the interlayer 202 and the lower layer 203 comprise glass, quartz or fused silica sheets that are chemically etched to form the channel 210 and other microfluidic conduits and connections. The upper layer 201, the interlayer 202 and the lower layer 203 may then be sealed by known joining steps. Notably, glass, quartz or fused silica are not "compliant," and cannot be deformed to make face seals. That is not a problem if the analysis is being done at lower temperatures (typically below 250° C.) where an intermediate layer of a compliant material such as polyimide can be added to the assembly. Conversely, these materials may be easier to work with when the deactivation layer is being applied.

In a representative embodiment, the channel 210 extends from interlayer upper surface 208 through interlayer lower surface 209 (i.e., through interlayer 202). As described more fully below, the channel 210 is sealed by securing the upper layer 201 over the interlayer upper surface 208 and by securing the lower layer 203 over the interlayer lower surface 209. In a representative embodiment, the channel 210, when sealed, has a substantially square cross-section. It is noted that this is merely illustrative and it is emphasized that the cross section of the sealed channel 210 may be of other shapes (e.g., a rectangle, an ellipse, a circle, etc.)

The serpentine shape of the channel 210 is selected to optimize the use of area of the microfluidic contaminant trap 200 of the representative embodiments. It is noted that the serpentine shape of the channel is merely illustrative, and the channel 210 may have other shapes, such as spiral or linear.

The length of the channel 210 and its cross-sectional area are selected to ensure substantial trapping of contaminants in the channel to substantially prevent contaminants from reaching the interlayer outlet, and therefore the column. Generally, the channel 210 has a cross-sectional area that is compatible with the internal diameter of the analytical column. Moreover, the channel 210 has a length selected to trap substantially all of the contaminants in the sample, with the length of the channel 210 being dependent on the type of solvent, injection volume, and type of contaminants, for example. Finally, the dimensions of the channel 210 are dependent on column operation (temperature programmed versus isothermal) as the dimensions of the microfluidic contaminant trap 200 will impact the chromatographic performance of the system. Generally, the degree of trapping of contaminants is dependent on various parameters, including but not limited to the solvent used, the injection volume of the sample, the number of sample injections and the temperature of the microfluidic contaminant trap.

Figure 2B:
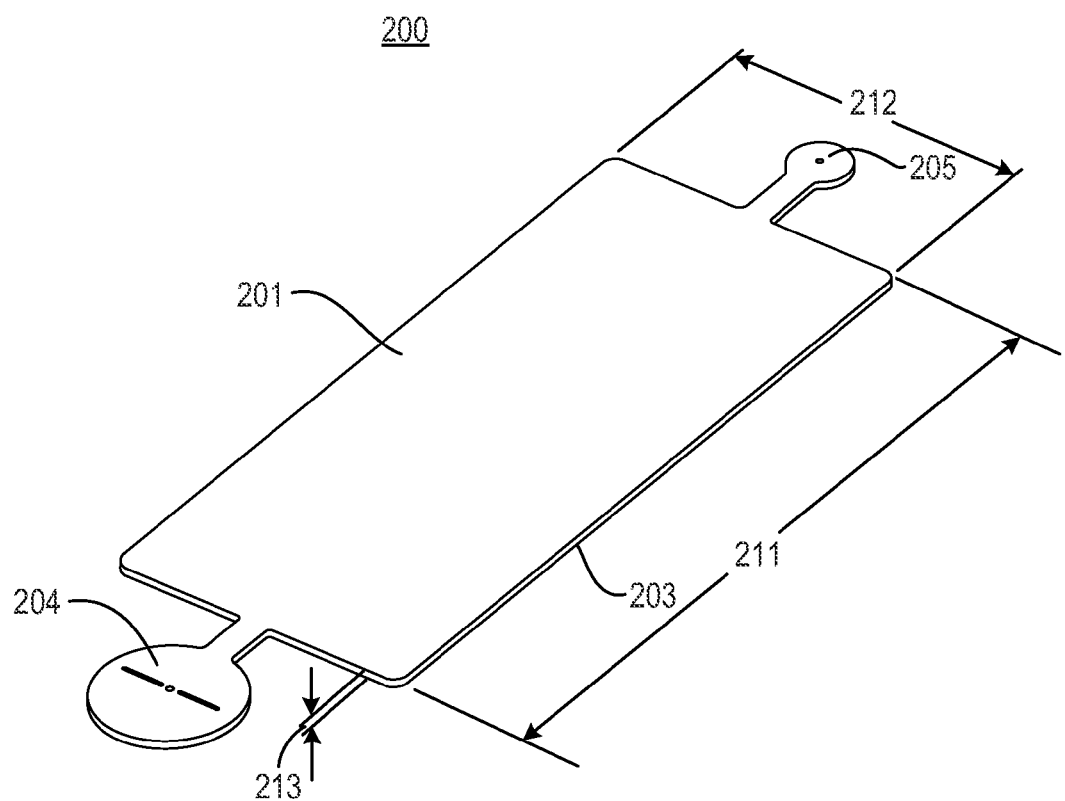
FIG. 2B is a perspective view of the microfluidic contaminant trap depicted in FIG. 2A.

FIG. 2B depicts the microfluidic contaminant trap 200 in a perspective view after sealing. In accordance with a representative embodiment, the upper layer 201, the interlayer 202 (not shown in FIG. 2B) and the lower layer 203 are made of the same material, whereas in other representative embodiments two or more materials may be used for these components of the microfluidic contaminant trap.

The overall structure of the microfluidic contaminant trap 200 is substantially planar with a length 211, a width 212 and a thickness 213. Beneficially, the planar structure of the microfluidic contaminant trap 200 fosters its coupling to a flat heater (e.g., a resistive heating element formed in aluminum nitride (AlN) to ensure efficient transfer of heat, a characteristic that is beneficial for rapid heating of the microfluidic contaminant trap.

In one representative embodiment, the upper layer 201, the interlayer 202 and the lower layer 203 are made of comparatively thin layers. Illustratively, the upper layer 201, the interlayer 202 and the lower layer 203 have thicknesses in the range of 10 μm to 1 mm of stainless steel that are diffusion bonded to form a substantially monolithic piece of metal with internal channels and smooth external surfaces. Illustratively, the microfluidic contaminant trap 200 is fluidly sealed by diffusion bonding the lower layer 203 to the interlayer lower surface 209, and by diffusion bonding the interlayer upper surface 208 to the upper layer 201. Notably, the seal created between the interlayer upper surface 208 to the upper layer 201 provides a seal for the inlet 204 on one end of the channel 210, for the outlet 205 at the other end of the channel 210, and all points therebetween. In a representative embodiment, the bonding of the lower layer 203 to the interlayer 202 and the upper layer 201 may be effected as described in commonly owned U.S. Pat. No. 6,783,871, the disclosure of which is specifically incorporated herein by reference. Alternatively, the lower layer 203, the interlayer 202 and the upper layer 201 may be brazed using suitable brazing foil layers between the lower layer 203, the interlayer 202 and the upper layer 201.

The various features (e.g., the channel 210, the inlet 204, the outlet 205 and the connections therebetween) are made using one of known photochemical machining/etching techniques within the purview of one or ordinary skill in the art. Alternatively, the various features may be fabricated using a known laser machining technique.

It is emphasized that the use of stainless steel for the upper layer 201, the interlayer 202 and the lower layer 203 is merely illustrative. Alternatively, the upper layer 201, the interlayer 202 and the lower layer 203 may be formed of one or more of titanium, nickel, quartz, fused silica, glass, or silicon. In a specific embodiment a deactivation coating may be applied over the surfaces of the channel 210, and as applicable, to the trapping features, to reduce the interaction of analytes of the sample with the surfaces with which the sample contacts. As noted above, the deactivation coating comprises a selected chemical substance useful in reducing the interaction of the surfaces of the microfluidic contaminant trap with the analyte of interest within the sample. Additionally, particles can be provided in the channel 210 to provide a comparatively increased surface area to improve trapping of contaminants in the microfluidic contaminant trap 200. Additional features can be included in the channel 210 to spread out the trapped contaminants through the channel 210.

The following examples provide illustrative dimensions of the microfluidic contaminant trap 200 and components thereof based on application. These examples are merely illustrative and are in no way limiting of the present teachings.

EXAMPLE 1

In a first example, the microfluidic trap 200 has dimensions (length 211×width 212×thickness 213) of 45 mm×20 mm×1 mm. The channel 210 has an inlet to outlet length of 793 mm, and a width of 500 μm and a height of 500 μm.

EXAMPLE 2

In a second example, the microfluidic contaminant trap 200 has dimensions of has dimensions (length 211×width 212×thickness 213) of 45 mm×2 mm×1 mm, and the channel 210 has dimensions (L×W×H) of 60 mm×250 μm×250 μm.

EXAMPLE 3

In a third example, the microfluidic contaminant trap 200 has dimensions of has dimensions (length 211×width 212×thickness 213) of 45 mm×2 mm×1 mm, and the channel 210 has dimensions (L×W×H) of 60 mm×250 μm×250 μm with a tube brazed to the inlet 204.

EXAMPLE 4

In a fourth example, the microfluidic contaminant trap 200 has dimensions (length 211×width 212×thickness 213) of 45 mm×40 mm×1 mm, and the channel 210 has dimensions (L×W×H) of 1.6 m×500 μm×500 μm.

Referring again to FIG. 2B, one clear benefit of this embodiment of the microfluidic contaminant trap 200 is the ease of its connection to the outlet of the sample inlet 101 and to the column. Notably, in the presently described representative embodiment, the inlet 204 connects directly to the bottom of the outlet of the sample inlet 101. This connection is a so-called "face seal" that directly connects the microfluidic contaminant trap 200 to the outlet of the sample inlet 101 without the need of a ferrule. In a particular embodiment with a S/SL. inlet, this face seal would replace the normally used gold seal and ferrule connection. In an embodiment with a multimode inlet (MMI), this face seal would connect directly to the bottom of the inlet and thus replace the ferrule connection. Similarly, the outlet 205 is connected to the column 103 using a face seal. Further details of the connection of the inlet 204 to the outlet of the sample inlet 101 and the outlet 205 to the column 103 are described in concurrently filed and commonly owned U.S. patent application No. 14/057,016 entitled "GC Column Connection with a Planar Connection to Mating Devices," naming George Walsh, et al. inventors. The entire disclosure of U.S. patent application No. 14/057,016is specifically incorporated herein by reference. Notably, this application specifically includes an illustration of an MMI to trap connection. It is noted that so-called "face seals" provided by the microfluidic contaminant trap 200 are merely illustrative and in no way limiting. Notably, there are other known methods to effect fluid connections to microfluidic plates. For example, fittings can be welded or brazed to the plate that allow connection to tubular devices, including fused silica capillary columns.

In a representative embodiment, the microfluidic contaminant trap 200 can be heated or cooled, or both, separately from the sample inlet and the analytical column. This allows the initial temperature of the microfluidic contaminant trap 200 to be maintained below the solvent boiling point at the beginning of the analysis, while also allowing the microfluidic contaminant trap 200 to be heated to the maximum temperature of the analytical method. In some cases, the microfluidic contaminant trap might be heated to a temperature higher than the maximum column temperature to enable back-flushing from the trap.

Figure 3:
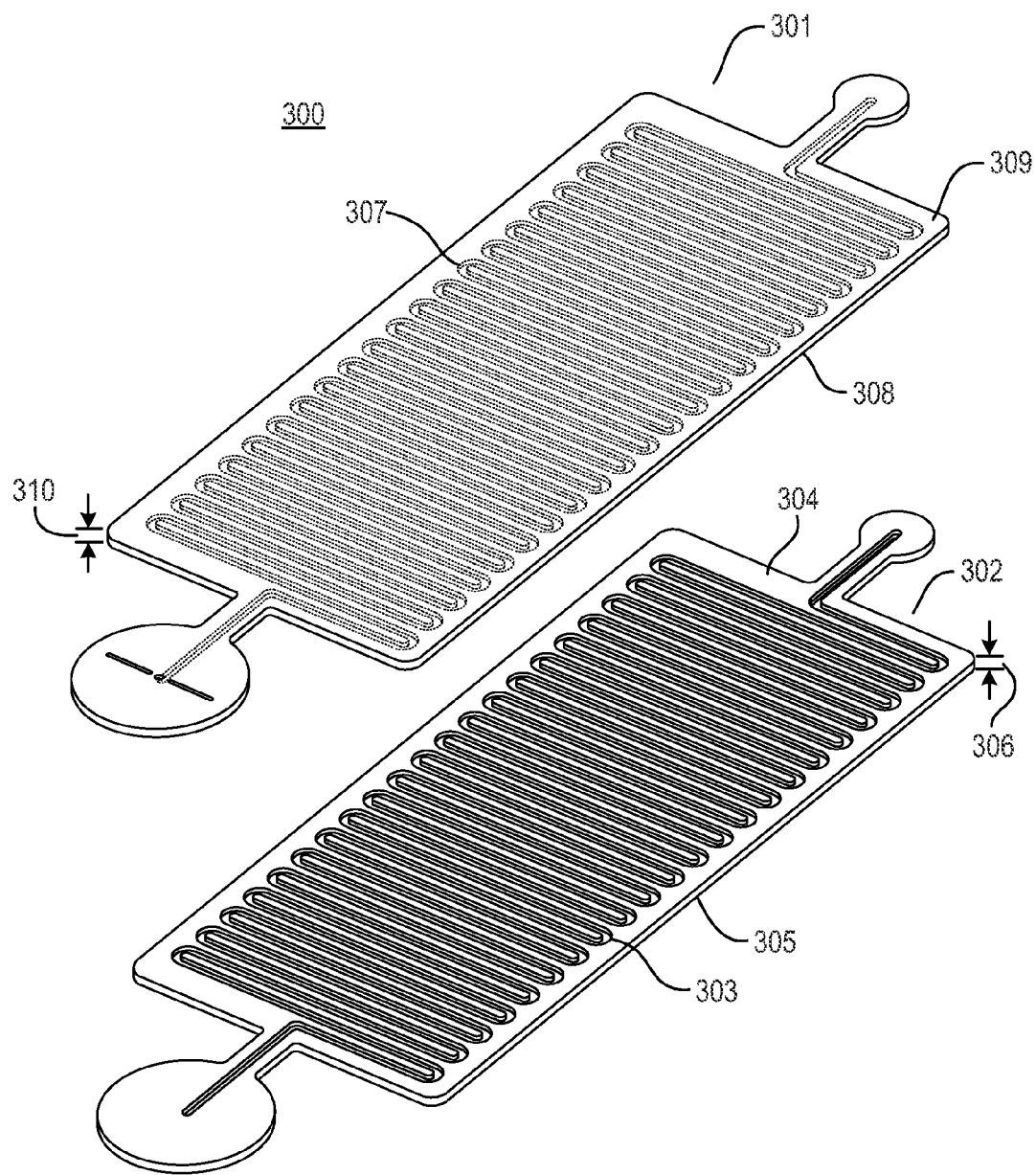
FIG. 3 is an exploded view of a microfluidic contaminant trap in accordance with a representative embodiment.

As noted above, in certain representative embodiments, the channel 210 extends from interlayer upper surface 208 through interlayer lower surface 209. However, this is not essential, and the channel can be formed by providing a "half-etched" channel in the interlayer and a "half-etched" channel in another layer. FIG. 3 depicts a microfluidic contaminant trap 300 in accordance with such an embodiment. Notably, many of the details of the materials, structure, features, dimensions and methods of fabrication described above in connection with the representative embodiments of FIG. 1~2B are common to the description of the representative embodiments of FIG. 3. Often, these details are not repeated in order to avoid obscuring the description of the representative embodiment of FIG. 3.

The microfluidic contaminant trap 300 comprises an upper layer 301 and an interlayer 302. In this representative embodiment, the interlayer 302 comprises a first channel 303 provided in an upper surface 304. The first channel 303 does not extend through to a lower surface 305 of the interlayer 302, but rather is provided only partially into the interlayer 302. For example, the first channel 303 may be provided in the interlayer 302 with a depth that is approximately one-half a thickness 306 of the interlayer. Moreover, the first channel 303 is, in cross-section, one-half the shape of the channel 210 described above. So, continuing with the illustrative shapes described above, the first channel 303 has a cross-section of one-half of a square, or one-half of an ellipse, or one-half of a circle, for example. The other "half" of the shape is provided by a second channel 307 (shown in phantom) provided in the upper layer 301. Specifically, the second channel 307 is provided only partially into a lower surface 308 of the upper layer 301. So, the second channel 307 does not extend through an upper surface 309 of the upper layer 301, but rather is provided only partially into the upper layer 301. For example, the second channel 307 may be provided in the upper layer 301 with a depth that is approximately one-half a thickness 310 of the upper layer 301. Moreover, the second channel 307 is, in cross-section, one-half the shape of the channel 210 described above. So, continuing with the illustrative shapes described above, the second channel 307 has a cross-section of one-half of a square, or one-half of an ellipse, or one-half of a circle, for example.

The second channel 307 of the upper layer 301 and the first channel 303 of the interlayer 302 are formed in an aligned manner and are mirror-images of one another, so that when the upper surface 304 of the interlayer 302 contacts lower surface 308 of the upper layer 301, the first channel 303 is aligned with the second channel 307 and each "half" of the cross-sectional shape of the first channel 303 and the second channel 307 are joined to form a "whole" cross-sectional shape channel. Continuing the illustration from above, if the first channel 303 and the second channel 307 had cross-sectional shapes that were complementary half-squares, upon contacting the upper layer 301 with the interlayer 302, the channel that results from first channel 303 and second channel 307 has a square-shaped cross-section.

After the upper layer 301 and the interlayer 302 are brought in contact, they are bonded together to form microfluidic contaminant trap 300 that is fluidically sealed. The bonding method used depends on the materials selected for the upper layer 301 and interlayer 302, and are as described above in connection with the representative embodiments in FIGS. 2A-2B. Among other benefits, the unbonded upper layer 301 and interlayer 302 are comparatively strong compared to so-called "through-etched" designs. Specifically, in known structures, etching through the layers to create channels typically results in channel walls that are cantilevered out from the layer sides. These channel walls are weaker than a wall that rises up from a partially etched layer. Moreover, the unbonded upper layer 301 and interlayer 302 allow for the design of longer channels and therefore a longer (and more effective) contaminant trap. Notably, if the first and second channels 303, 307 are formed by chemically etching the upper layer 301 and the interlayer 302, this microfluidic contaminant trap 300 has comparatively rough surfaces. Beneficially, the comparatively rough surfaces of the first channel 303 and the second channel 307 provide increased surface area to capture contaminants more effectively, and may slow the flow of the sample, resulting in more efficient trapping.

It is noted that in certain representative embodiments, the second channel 307 in the upper layer 301 is foregone, and the lower surface 308 of the upper layer 301 is substantially flat. In such an embodiment, the channel comprises only the first channel 303 provided in the interlayer 302 with the cross-sectional area of the first channel selected for the application. The lower surface 308 of the upper layer 301 contacts the upper surface 304 of the interlayer 302, and the two surfaces are bonded together as described above to provide a gas impermeable seal of the channel.

Figure 4:
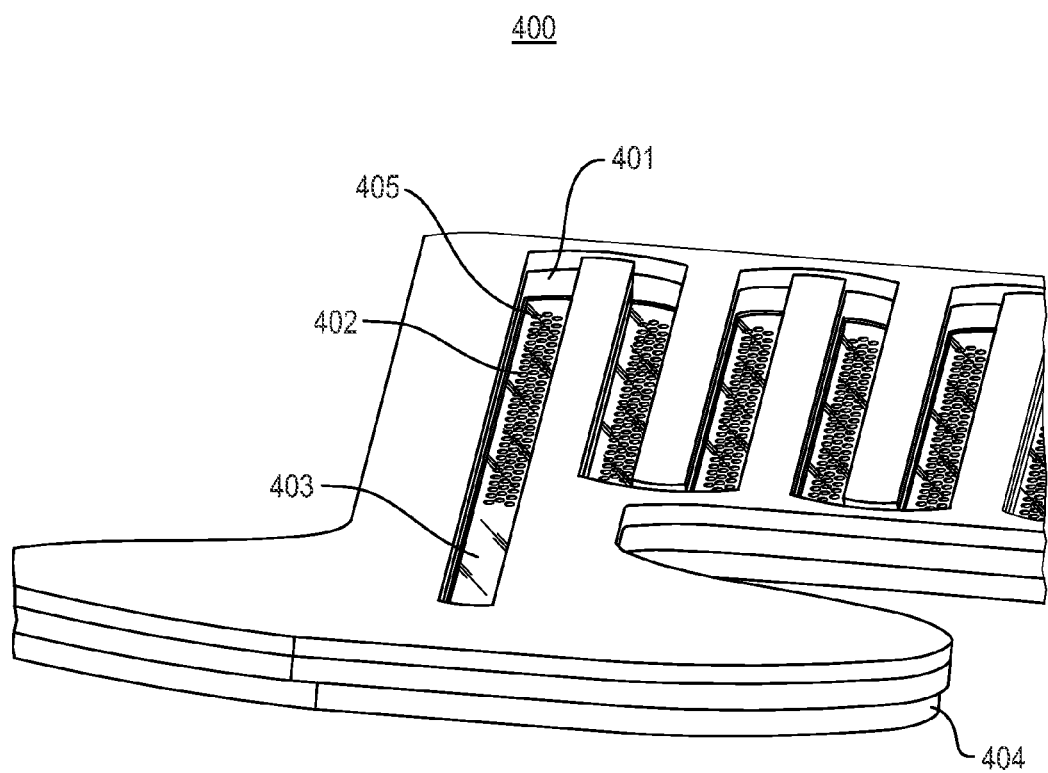
FIG. 4 is a perspective view of a portion of a microfluidic contaminant trap in accordance with a representative embodiment.

As noted above, it is useful to provide trapping features to improve the effectiveness of the channels in the microfluidic contaminant traps of the present teachings. FIG. 4 depicts one structure useful as trapping features.

FIG. 4 is a perspective view of a portion of a microfluidic contaminant trap 400 in accordance with a representative embodiment. Many of the details of the materials, structure, features, dimensions and methods of fabrication described above in connection with the representative embodiments of FIG. 1~3 are common to the description of the representative embodiments of FIG. 4. Often, these details are not repeated in order to avoid obscuring the description of the representative embodiment of FIG. 4.

Microfluidic contaminant trap 400 comprises a channel 401 having a serpentine path between an inlet (not shown) and an outlet (not shown). The channel 401 has trapping features 402 provided along a surface 403 of the channel 401. In the representative embodiment depicted in FIG. 4, trapping features 402 provide additional surface area, to slow the sample flow and/or to mechanically trap contaminants, resulting in more efficient trapping. In the depicted embodiment, the trapping features 402 are "microposts" or cylindrical extensions from the surface 403. Alternatively, the trapping features 402 may be cylindrical recesses in the surface 403. Notably, the cylindrical shape of the trapping features 402 is merely illustrative, and similar trapping features can be provided on/in the surface 403 having different shapes, irregular shapes, and combinations of shapes. Illustratively, the microposts have a height that is approximately 5% of the height of the channel 401. However, the microposts could be larger or smaller than this illustrative height, and are limited by the ability to fabricate the trapping features 402.

Furthermore, in addition to or instead of trapping features 402 depicted in FIG. 4, a coating 405 may be provided over the surface 403 of the channel 401, as well as any interior or exterior features of the microfluidic contaminant trap that come in contact with the sample. As alluded to above, the coating 405 is provided to reduce the interaction of the surfaces with the analyte of interest within the sample. The coating 405 comprises a selected chemical substance useful in reducing the interaction of the surfaces with the analytes of the sample.

In a representative embodiment, the coating 405 comprises a functionalized hydrogenated amorphous silicon surface, such as described, for example in U.S. Pat. No. 6,444,326, to Smith. The disclosure of U.S. Pat. No. 6,444,326 is specifically incorporated herein by reference. In a second representative embodiment, the coating 405 comprises a silicon carbide surface, such as described, for example in U.S. Pat. No. 4,532,150, to Endo et al. The disclosure of U.S. Pat. No. 4,532,150 is specifically incorporated herein by reference. In a third representative embodiment, the coating 405 comprises a siloxane surface, such as described, for example in U.S. Pat. No. 4,376,641, to Nestrick et al. The disclosure of U.S. Pat. No. 4,376,641 is specifically incorporated herein by reference. Illustratively, the deactivation coating may be a known silicon-based coating, a known siloxane, or other known polymeric, monomeric, or carbide coatings. The coating is applied by known methods, and is applied after various components of the microfluidic contaminant trap are bonded to one another to ensure all surfaces that come into contact with the analytes of the sample are properly coated.

In certain embodiments, the channel 401 extends through an interlayer (e.g., such as embodiments described in connection with FIG. 2A), whereas in other embodiments the channel 401 may be one-half of the channel (e.g., such as embodiments described in connection with FIG. 3), and the channel is formed by mating an upper layer to an interlayer. The representative embodiment depicts the former structure, and the trapping features 402 are formed on an inner surface of a lower layer 404. Alternatively, the trapping features may be formed on an inner surface of an upper layer (e.g., upper layer 201 of FIG. 2A). Still alternatively, the trapping features 402 may be formed on both the lower layer 404 and an upper layer (not shown in FIG. 4) to further increase the surface area over which the sample flows.

In other embodiments, the channel 401 may be etched only part-way into the first channel of the interlayer (e.g., first channel 303 of FIG. 3) or part-way into the channel of the upper layer (e.g., second channel 307 of FIG. 3), or both.

Figure 5:
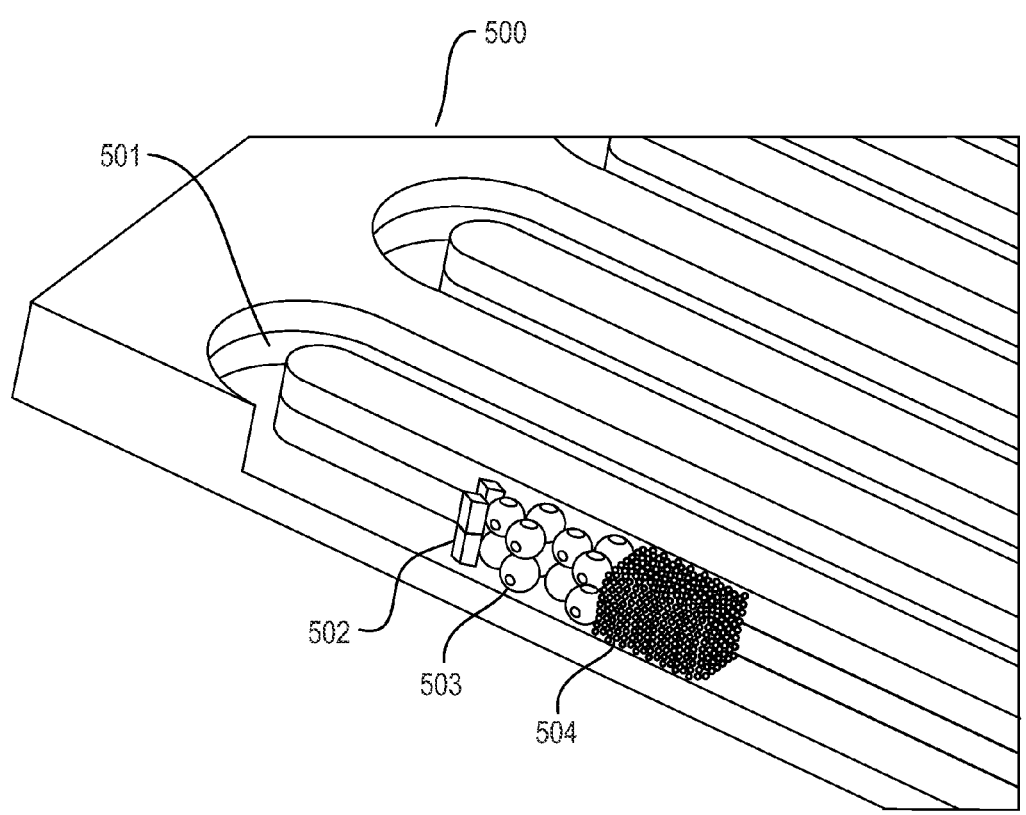
FIG. 5 is a perspective view of a portion of a microfluidic contaminant trap in accordance with a representative embodiment.

As an alternative or in addition to trapping features formed in the channel(s) of a microfluidic contaminant trap, GC column packing material may be provided in the channel. FIG. 5 is a perspective view of a portion of a microfluidic contaminant trap 500 in accordance with a representative embodiment. Many of the details of the materials, structure, features, dimensions and methods of fabrication described above in connection with the representative embodiments of FIG. 1~4 are common to the description of the representative embodiments of FIG. 5. Often, these details are not repeated in order to avoid obscuring the description of the representative embodiment of FIG. 5.

The microfluidic contaminant trap 500 comprises a channel 501 having first packing material 502, second packing material 503 and third packing material 504. The packing material may be selected from a number of packing materials known to one of ordinary skill in the art. Illustratively, the first packing material 502, the second packing material 503 or the third packing material 504 may be made of metal, ceramic, or glass, or could be polymeric or carbonaceous packing materials. It is noted that the use of first, second and third packing materials 502~504 is merely illustrative and more or fewer types of packing material may be provided in the channel 501. Moreover, the volume of the channel 501 occupied by the first, second and third packing materials 502~504 is selected based on various factors, and can be greater or less than that depicted in FIG. 5. Like trapping features described above, the first, second and third packing materials 502~504 provide increased surface area to capture contaminants more effectively, and may slow the flow of the sample, resulting in more efficient trapping.

Figure 6:
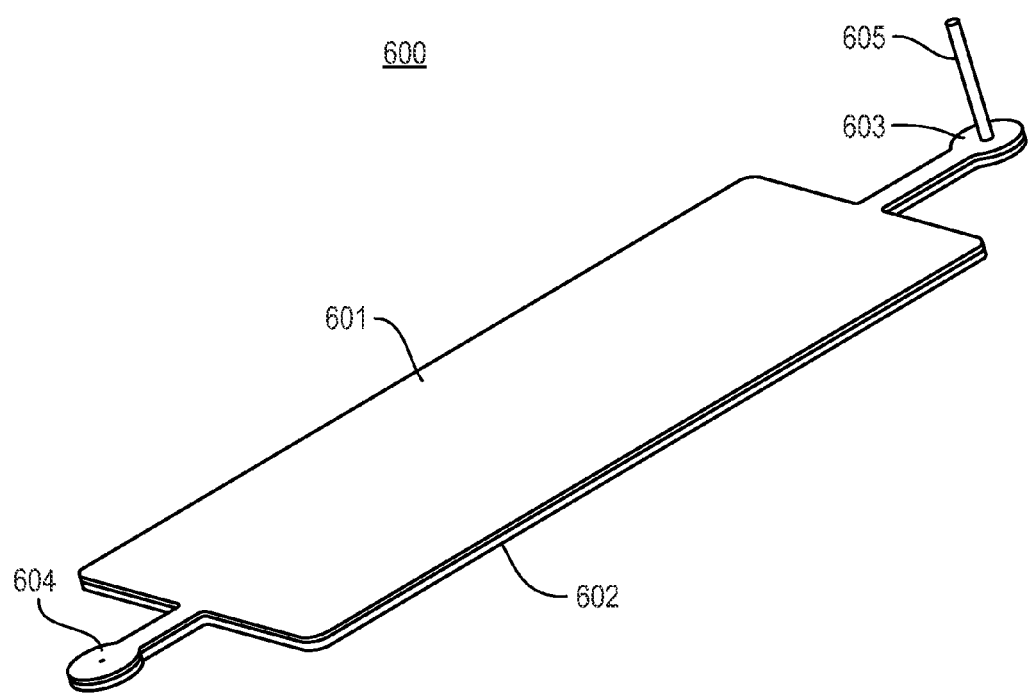
FIG. 6 is a perspective view of a microfluidic contaminant trap in accordance with a representative embodiment.

The microfluidic contaminant traps of the representative embodiments provide versatility of use in many ways. FIG. 6 is a perspective view of a microfluidic contaminant trap 600 in accordance with a representative embodiment. Many of the details of the materials, structure, features, dimensions and methods of fabrication described above in connection with the representative embodiments of FIG. 1~5 are common to the description of the representative embodiments of FIG. 6. Often, these details are not repeated in order to avoid obscuring the description of the representative embodiment of FIG. 6.

Microfluidic contaminant trap 600 comprises an upper layer 601, a lower layer 602, an inlet 603 and an outlet 604. The microfluidic contaminant trap 600 could be joined with additional parts, such as a tube 605, to provide additional functionality. In the representative embodiment of FIG. 6, the microfluidic contaminant trap 600 is laser welded to tubing 605 that is part of the interface to a GC sample inlet. The function of the tube 605 is to relocate the point where the sample enters the microfluidic trap. It is notable that this tube 605 does not form the seal between the microfluidic trap and the inlet; a face seal is made between the two. The capillary column will again connect via one of the new capillary to face seal fittings to outlet 604. The tube on the inlet side can be brazed or welded in place.

As noted above, more than one interlayer may be implemented in microfluidic contaminant traps of the representative embodiments. Among other benefits, the overall channel length within the trap could be made longer without increasing the area ("footprint") of the microfluidic contaminant trap.

Figure 7:
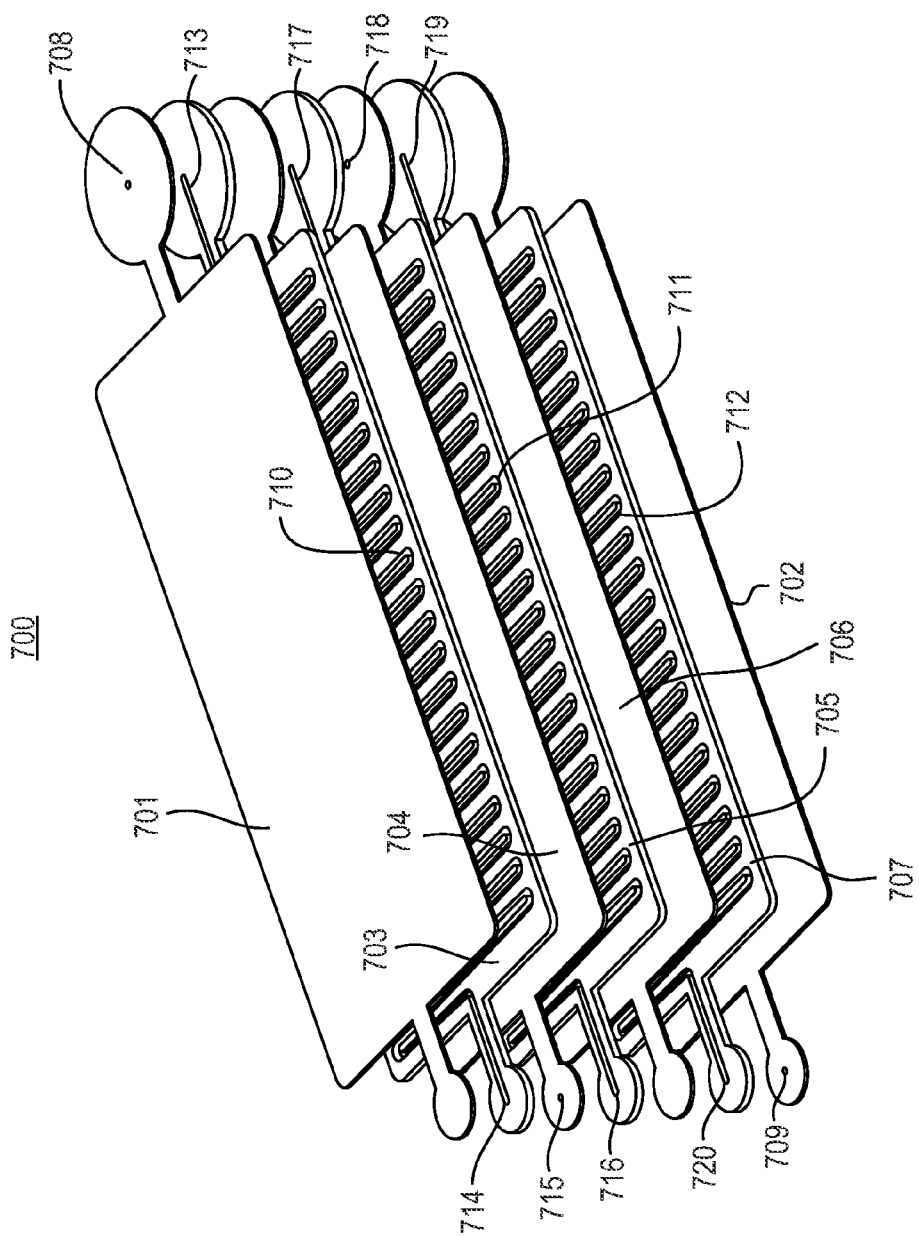
FIG. 7 is an exploded view of a microfluidic contaminant trap in accordance with a representative embodiment.

FIG. 7 is an exploded view of a microfluidic contaminant trap 700 in accordance with a representative embodiment. Many of the details of the materials, structure, features, dimensions and methods of fabrication described above in connection with the representative embodiments of FIG. 1~6 are common to the description of the representative embodiments of FIG. 7. Often, these details are not repeated in order to avoid obscuring the description of the representative embodiment of FIG. 7.

The microfluidic contaminant trap 700 comprises an upper layer 701 and an opposing lower layer 702. Between the upper layer 701 and the lower layer 702, the microfluidic contaminant trap 700 comprises a first channel layer 703, a first layer 704, a second channel layer 705, a second layer 706 and a third channel layer 707. The microfluidic contaminant trap 700 comprises an inlet 708 that is fluidly connected to an outlet 709. In a manner similar to that described in connection with the embodiments of FIGS. 2A and 2B, first, second and third channel layers 703, 705 and 707, are sealed by the upper layer 701, the lower layer 702, the first layer 704 and the second layer 706. So, for example, first channel 710 is sealed by the bonding of the upper layer 701 and the first layer 704 on opposing sides of the first channel layer 703.

The fluid connection between the inlet 708 and the outlet 709 is provided by connections between the first channel 710 of first channel layer 703, second channel 711 of second channel layer 705 and third channel 712 of the third channel layer 707. Specifically, a first connection 713 disposed in the first channel layer 703 fluidly couples the inlet 708 to the first channel 710. A second connection 714 disposed at the opposing end of the first channel layer 703 fluidly connects the first channel 710 to the second channel 711. Fluid flows through a first opening 715 provided in the first layer 704 to a third connection 716 disposed in the second channel layer 705. A third connection 717 at the opposing end of the second channel layer fluidly connects the second channel 711 to the third channel 712 via a second opening 718 provided in the second layer 706 that is fluidly coupled to a fourth connection 719 provided in the third channel layer 707. A fourth connection 720 is fluidly connected to the third channel 712, and after traversing the third channel 712, fluid is provided to the outlet 709. Typically, the connections and openings have a cross-sectional area that is similar to that of the channels. However, the cross-sectional areal dimensions of the connections and openings can differ from the channel dimensions as needed for a particular mechanical design. For example, a very narrow channel may have a larger opening to connect to external devices because a hole the size of the small channel could not be located precisely enough to ensure alignment with the mating device. So, by way of illustration a 250 um×250 um channel may have a 500 um diameter opening.

The various connections and openings in the layers depicted in FIG. 7 are formed in the same manner as the channels formed therein, using known techniques such as noted above. As such, vertical (perpendicular to the plane of the layers depicted in FIG. 7) and horizontal fluid connections are made directly in the layers of the microfluidic contaminant trap 700 and enable the connection of a plurality of channel layers in a comparatively small area.

In another representative embodiment, a microfluidic contaminant trap may comprise two independent elements that are fluidly isolated from one another. For example, a cooling device may be thermally coupled to a microfluidic contaminant trap, but be fluidly isolated.

Figure 8:
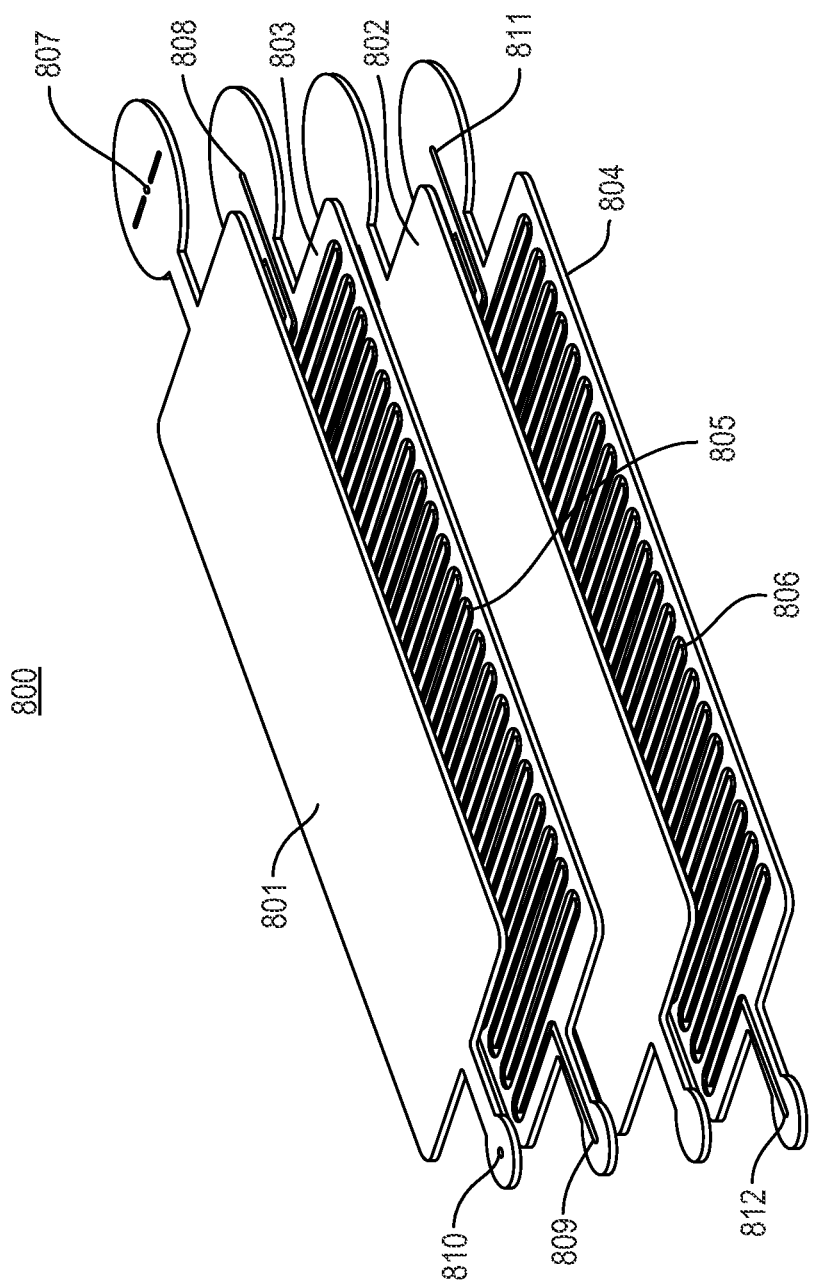
FIG. 8 is an exploded view of a microfluidic contaminant trap in accordance with a representative embodiment.

FIG. 8 is an exploded view of a microfluidic contaminant trap 800 in accordance with a representative embodiment. Many of the details of the materials, structure, features, dimensions and methods of fabrication described above in connection with the representative embodiments of FIG. 1~7 are common to the description of the representative embodiments of FIG. 8. Often, these details are not repeated in order to avoid obscuring the description of the representative embodiment of FIG. 8.

The microfluidic contaminant trap 800 comprises a first layer 801 and a second layer 802, which provide sealing and fluid isolation to a first channel layer 803 and a second channel layer 804. The first and second channel layers 803, 804 each comprise a first channel 805 and a second channel 806, respectively, In the representative embodiments described in connection with FIG. 8, the first and second channels 805, 806 are provided part-way through the thickness of their respective layers. In certain embodiments, first and second channels 805, 806 have cross-sections that are "one-half" of a geometric shape (e.g., one-half of a circle). Alternatively, like certain embodiments described in connection with FIG. 3 first and second channels 805, 806 may be coupled to complementary channels (not shown in FIG. 8A) disposed in first layer 801 and second layer 802, respectively.

In yet further embodiments, like certain embodiments described in connection with FIG. 2A, the first channel 805 and the second channel 806 may be etched from one side through to another side of first and second layer 801, 802, respectively. In such embodiments, the first and second channels 805, 806 are fluidly sealed and fluidly isolated from one another.

In a representative embodiment, a first inlet 807 receives a fluid (e.g., a sample), and transfers the fluid to a first connection 808 to the first channel 805. The fluid flows through the first channel 805 and is provided by a second connection 809 to a first outlet 810. A second inlet 811 receives a fluid and transfers the fluid to the second channel 806. The fluid flows through the second channel 806 and is provided to a second outlet 812.

In a representative embodiment, the fluid provided to the first inlet 807 is a sample, and the fluid provided to the second inlet 811 is a cooling fluid or a heating fluid. Because the first channel 805 and the second channel 806 are fluidly isolated but thermally connected, the cooling or heating fluid flowing in the second channel 806 can be used to set or alter the temperature of the sample flowing in the first channel 805. So, for example, a cooling fluid can be used to cool the whole trap and thus the sample. Alternatively, the channel for the cooling fluid could be routed under only one section of the sample channel and the cooling fluid could be set to a temperature below the vaporization temperature of the solvent. This would cause the sample to re-condense, Then, the trap could be heated rapidly to inject the sample into the column.

In view of this disclosure it is noted that the methods and devices can be implemented in keeping with the present teachings. Further, the various components, materials, structures and parameters are included by way of illustration and example only and not in any limiting sense. In view of this disclosure, the present teachings can be implemented in other applications and components, materials, structures and equipment needed to implement these applications can be determined, while remaining within the scope of the appended claims.

The invention claimed is:

1. A microfluidic contaminant trap, comprising:
    an inlet configured to connect directly or indirectly to a sample inlet of a gas chromatography (GC) system;
    an outlet configured to connect directly to an inlet of a GC column or indirectly to the GC column via another fluidic component;
    an interlayer comprising a channel for trapping contaminants;
    an upper layer disposed over and bonded to the interlayer; and
    a coating disposed over the channel, wherein coating reduces interactions of analytes from a sample provided at the inlet of the microfluidic contaminant trap.

2. A microfluidic contaminant trap as claimed in claim 1, wherein the upper layer is substantially planar.

3. A microfluidic contaminant trap as claimed in claim 1, wherein the bonded upper layer provides a substantially impermeable gas seal of the channel at an upper surface of the interlayer.

4. A microfluidic contaminant trap as claimed in claim 1, further comprising a lower layer disposed beneath the interlayer and bonded thereto.

5. A microfluidic contaminant trap as claimed in claim 4, wherein bonded lower layer provides a substantially impermeable gas seal of the channel at a lower surface of the interlayer.

6. A microfluidic contaminant trap as claimed in claim 4, wherein the channel extends from an upper surface of the interlayer through a lower surface of the interlayer.

7. A microfluidic contaminant trap as claimed in claim 1, wherein the channel is a first channel, and the microfluidic contaminant trap further comprises an upper layer disposed over the interlayer, the upper layer comprising a second channel that is aligned over the first channel.

8. A microfluidic contaminant trap as claimed in claim 7, wherein the first channel and the second channel are complementary, and the upper layer is configured to seal the channel.

9. A microfluidic contaminant trap as claimed in claim 1, further comprising trapping features in the channel, wherein the channel features provide additional surface area in the channels to trap the contaminants.

10. A microfluidic contaminant trap as claimed in claim 9, wherein the trapping features comprise posts formed in the channel.

11. A microfluidic contaminant trap as claimed in claim 1, wherein the microfluidic contaminant trap comprises one of: stainless steel; titanium; nickel; quartz; fused silica; glass; or silicon.

12. A microfluidic contaminant trap as claimed in claim 1, further comprising a packing material disposed in the channel, wherein the packing material provides additional surface area in the channels to trap the contaminants.

13. A microfluidic contaminant trap as claimed in 1, wherein the coating comprises one of functionalized hydrogenated amorphous silicon, silicon carbide, or siloxane.

14. A microfluidic contaminant trap, comprising:
    an inlet configured to connect directly or indirectly to a sample inlet of a gas chromatography (GC) system;
    an outlet configured to connect either directly or indirectly to an inlet of a GC column;
    a first interlayer comprising a first channel;
    a first coating disposed over the first channel, wherein the first coating reduces interactions of analytes from a sample provided at the inlet of the microfluidic contaminant trap;
    a second interlayer comprising a second channel, wherein the first channel is in fluid communication with the second channel;
    a second coating disposed over the second channel, wherein the second coating reduces interactions of analytes from the sample provided at the inlet of the microfluidic contaminant trap;
    an upper layer disposed over the first interlayer;
    a middle layer disposed between a lower surface of the first interlayer and above an upper surface of the second interlayer; and
    a lower layer disposed beneath the second interlayer, wherein the upper layer and the middle layer are configured to seal the first channel and the middle layer and the lower layer are configured to seal the second channel.

15. A microfluidic contaminant trap as claimed in claim 14, wherein the first channel extends from an upper surface of the first interlayer through the lower surface of the first interlayer.

16. A microfluidic contaminant trap as claimed in claim 15, wherein the second channel extends from the upper surface of the second interlayer to a lower surface of the second interlayer.

17. A microfluidic contaminant trap as claimed in claim 14, further comprising first trapping features in the first channel and second trapping features in the second channel, wherein the first and second channel features provide additional surface area in first and second channels, respectively, to trap the contaminants.

18. A microfluidic contaminant trap as claimed in claim 17, wherein at least one of the first and second trapping features comprise posts.

19. A microfluidic contaminant trap as claimed in claim 14, wherein the microfluidic contaminant trap comprises one of: stainless steel; titanium; nickel; quartz; fused silica; glass; or silicon.

20. A microfluidic contaminant trap as claimed in claim 14, further comprising a packing material disposed in at least one of the first and second channels, wherein the packing material provides additional surface area in the channels to trap the contaminants.

* * * * *

UNITED STATES PATENT AND TRADEMARK OFFICE
CERTIFICATE OF CORRECTION

| | | |
|---|---|---|
| PATENT NO. | : 9,664,598 B2 | Page 1 of 1 |
| APPLICATION NO. | : 14/057022 | |
| DATED | : May 30, 2017 | |
| INVENTOR(S) | : George P. Walsh et al. | |

It is certified that error appears in the above-identified patent and that said Letters Patent is hereby corrected as shown below:

On the Title Page

On the page 3, in Column 1, under "Other Publications", Line 3, delete "Protoype" and insert -- Prototype --, therefor.

In the Specification

In Column 5, Line 46, delete "Smith," and insert -- Smith. --, therefor.

In Column 6, Line 8, delete "205," and insert -- 205. --, therefor.

In Column 9, Line 3, delete "S/SL." and insert -- S/SL --, therefor.

In Column 9, Line 4, delete "ferulle" and insert -- ferrule --, therefor.

In Column 9, Line 15, delete "14/057,016is" and insert -- 14/057,016 is --, therefor.

In Column 14, Line 55, delete "re-condense," and insert -- re-condense. --, therefor.

In the Claims

In Column 15, Line 13, in Claim 1, after "wherein" insert -- the --.

In Column 15, Line 55, in Claim 12, delete "channels" and insert -- channel --, therefor.

In Column 16, Line 1, in Claim 13, after "in" insert -- claim --.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*